United States Patent [19]
Cherry et al.

[11] Patent Number: 5,968,883
[45] Date of Patent: Oct. 19, 1999

[54] PEROXIDASE VARIANTS

[75] Inventors: Joel R. Cherry, Davis, Calif.; Allan Svendsen, Birkerød, Denmark; Ture Damhus, Copenhagen Ø, Denmark; Palle Schneider, Ballerup, Denmark

[73] Assignee: Novo Nordisk A/S, Bagsvaerd, Denmark

[21] Appl. No.: 09/235,736

[22] Filed: Jan. 22, 1999

Related U.S. Application Data

[63] Continuation of application No. PCT/DK97/00361, Sep. 2, 1997.

[30] Foreign Application Priority Data

Sep. 3, 1996 [DK] Denmark .................................. 0937/96

[51] Int. Cl.$^6$ ................ C11D 7/42; C11D 7/54; C12N 9/08
[52] U.S. Cl. ................ 510/305; 510/374; 510/392; 435/192

[58] Field of Search ..................... 435/189, 190, 435/192; 510/226, 320, 321, 305, 374, 375, 530

[56] References Cited

U.S. PATENT DOCUMENTS 5,817,495 10/1998 Pedersen et al. ..................... 435/192
5,851,811 12/1998 Welinder et al. ..................... 435/192

FOREIGN PATENT DOCUMENTS

WO 89/09813 10/1989 WIPO.
WO 91/05839 5/1991 WIPO.
WO 93/24618 12/1993 WIPO.
WO 95/10602 4/1995 WIPO.

*Primary Examiner*—Yogendra Gupta
*Assistant Examiner*—Dawn L. Garrett
*Attorney, Agent, or Firm*—Steve T. Zelson, Esq.; Elias Lambiris, Esq.

[57] ABSTRACT

The present invention relates to novel variants of *Coprinus cinereus* peroxidase showing excellent hydrogen peroxide stability.

18 Claims, No Drawings

SEQUENCE LISTING

<160> NUMBER OF SEQ ID NOS: 1

<210> SEQ ID NO 1
<211> LENGTH: 343
<212> TYPE: PRT
<213> ORGANISM: Coprinus cinereus

<400> SEQUENCE: 1

```
Gln Gly Pro Gly Gly Gly Ser Val Thr Cys Pro Gly Gly Gln Ser
 1               5                  10                  15

Thr Ser Asn Ser Gln Cys Cys Val Trp Phe Asp Val Leu Asp Asp Leu
            20                  25                  30

Gln Thr Asn Phe Tyr Gln Gly Ser Lys Cys Glu Ser Pro Val Arg Lys
        35                  40                  45

Ile Leu Arg Ile Val Phe His Asp Ala Ile Gly Phe Ser Pro Ala Leu
    50                  55                  60

Thr Ala Ala Gly Gln Phe Gly Gly Gly Gly Ala Asp Gly Ser Ile Ile
65                  70                  75                  80

Ala His Ser Asn Ile Glu Leu Ala Phe Pro Ala Asn Gly Gly Leu Thr
                85                  90                  95
```

```
Asp Thr Val Glu Ala Leu Arg Ala Val Gly Ile Asn His Gly Val Ser
            100                 105                 110

Phe Gly Asp Leu Ile Gln Phe Ala Thr Ala Val Gly Met Ser Asn Cys
        115                 120                 125

Pro Gly Ser Pro Arg Leu Glu Phe Leu Thr Gly Arg Ser Asn Ser Ser
    130                 135                 140

Gln Pro Ser Pro Pro Ser Leu Ile Pro Gly Pro Gly Asn Thr Val Thr
145                 150                 155                 160

Ala Ile Leu Asp Arg Met Gly Asp Ala Gly Phe Ser Pro Asp Glu Val
                165                 170                 175

Val Asp Leu Leu Ala Ala His Ser Leu Ala Ser Gln Glu Gly Leu Asn
            180                 185                 190

Ser Ala Ile Phe Arg Ser Pro Leu Asp Ser Thr Pro Gln Val Phe Asp
        195                 200                 205

Thr Gln Phe Tyr Ile Glu Thr Leu Leu Lys Gly Thr Thr Gln Pro Gly
        210                 215                 220

Pro Ser Leu Gly Phe Ala Glu Glu Leu Ser Pro Phe Pro Gly Glu Phe
225                 230                 235                 240

Arg Met Arg Ser Asp Ala Leu Leu Ala Arg Asp Ser Arg Thr Ala Cys
                245                 250                 255

Arg Trp Gln Ser Met Thr Ser Ser Asn Glu Val Met Gly Gln Arg Tyr
            260                 265                 270

Arg Ala Ala Met Ala Lys Met Ser Val Leu Gly Phe Asp Arg Asn Ala
        275                 280                 285

Leu Thr Asp Cys Ser Asp Val Ile Pro Ser Ala Val Ser Asn Asn Ala
    290                 295                 300

Ala Pro Val Ile Pro Gly Gly Leu Thr Val Asp Asp Ile Glu Val Ser
305                 310                 315                 320

Cys Pro Ser Glu Pro Phe Pro Glu Ile Ala Thr Ala Ser Gly Pro Leu
                325                 330                 335

Pro Ser Leu Ala Pro Ala Pro
            340
```

PEROXIDASE VARIANTS

CROSS-REFERENCE TO RELATED APPLICATIONS

This application is a continuation of PCT/DK97/00361 filed Sep. 2, 1997 which claims priority under 35 U.S.C. 119 of Danish application 0937/96 filed Sep. 3, 1996, the contents of which are fully incorporated herein by reference.

FIELD OF INVENTION

The present invention relates to novel variants of *Coprinus cinereus* peroxidase, and to bleaching and detergent compositions comprising such a peroxidase variant.

BACKGROUND OF THE INVENTION

The use of bleaching agents in washing procedures and as constituents of detergent compositions is well known in the art. Thus, bleaching agents are incorporated in or sold as constituents of a major part of the commercially available detergent compositions. Important conventional bleaching agents incorporated in detergent compositions are compounds which act as precursors of hydrogen peroxide formed in the course of the washing procedure. Perborates and percarbonates are the most important examples of compounds which are employed as bleaching agents and which exert a bleaching effect in this fashion.

It has been found that peroxidases, utilizing hydrogen peroxide as substrate, are able to enhance the bleaching effect of hydrogen peroxide during washing. The use of peroxidases for bleaching stains on fabrics is described in WO 89/09813. It has also been found that coloured substances leached from dyed fabrics can be bleached by means of peroxidases together with hydrogen peroxide. The use of peroxidases for inhibiting dye transfer in this way is described in WO 91/05839.

Variants of peroxidases which have a higher stability towards hydrogen peroxide than the wild type have also been described, see WO 93/24618 and WO 95/10602.

In WO 95/10602 it is shown that the *Coprinus cinereus* peroxidase variant (M242I+Y272F+E239K) has a good hydrogen peroxide stability at alkaline pH.

It is the purpose of this invention to create new *Coprinus cinereus* peroxidase variants which perform better than the ones previously disclosed at pH 7–10 and 30–50° C. (typical washing conditions).

SUMMARY OF THE INVENTION

It has surprisingly been found that a peroxidase variant with 3 or 7 mutations in regard to the wild-type *Coprinus cinereus* peroxidase has a surprising effect on the stability of the enzyme.

Accordingly the present invention relates to a peroxidase variant with improved hydrogen peroxide stability, wherein the following residues of the parent peroxidase, a *Coprinus cinereus* peroxidase encoded by the amino acid sequence shown in SEQ ID No. 1, are substituted as follows:
I49X+V53Y+T121Z+M166F+E239G+M242I+Y272F; or
I49X+V53Y+T121Z;
X being S, T, V, A or G; Y being G, A, S, T or H; and
Z being A, V, S, T or I.

In the present context the term "improved hydrogen peroxide stability " is intended to indicate that at least 50% of the activity of the peroxidase variant is present after treatment for 20 minutes in the presence of hydrogen peroxide at a concentration of 2.0 mM $H_2O_2$.

In the present context the term "improved hydrogen peroxide stability at alkaline conditions" is intended to indicate that at least 50% of the activity of the peroxidase variant is present after treatment for 20 minutes in the presence of hydrogen peroxide at a concentration of 2.0 mM $H_2O_2$, pH 10 and at 50° C.

In other aspects, the present invention relates to a bleaching composition comprising a peroxidase variant according to the invention and a hydrogen peroxide source, optionally additionally comprising an oxidizable substrate; and to a detergent composition comprising a surfactant, a peroxidase variant according to the invention and a hydrogen peroxide source, optionally additionally comprising an oxidizable substrate.

DETAILED DISCLOSURE OF THE INVENTION

In the present description and claims, the following abbreviations are used:
Amino Acids:

| | | |
|---|---|---|
| A | = Ala | = Alanine |
| V | = Val | = Valine |
| L | = Leu | = Leucine |
| I | = Ile | = Isoleucine |
| P | = Pro | = Proline |
| F | = Phe | = Phenylalanine |
| W | = Trp | = Tryptophan |
| M | = Met | = Methionine |
| G | = Gly | = Glycine |
| S | = Ser | = Serine |
| T | = Thr | = Threonine |
| C | = Cys | = Cysteine |
| Y | = Tyr | = Tyrosine |
| N | = Asn | = Asparagine |
| Q | = Gln | = Glutamine |
| D | = Asp | = Aspartic Acid |
| E | = Glu | = Glutamic Acid |
| K | = Lys | = Lysine |
| R | = Arg | = Arginine |
| H | = His | = Histidine |

In describing peroxidase variants according to the invention, the following nomenclature is used for ease of reference:
Original amino acid:position:substituted amino acid(s).

According to this nomenclature, for instance the substitution of lysine by serine in position 48 is as shown:
K48S
Multiple substitutions are separated by pluses, i.e.:
E214L+E239L
representing mutations in positions 214 and 239 substituting leucine for glutamic acid.

During the course of the study of creating peroxidase variants with excellent stability, it became clear that some mutations that improved stability of the peroxidase were also reducing the enzyme's catalytic activity.

One good example was the E239K mutation, which was found to have good stability (as disclosed in WO 95/10602), but which reduced the activity of the enzyme approximately 50% relative to the wild type enzyme when assayed at pH 7.

Thus, in combinatorial libraries that were screened for improved stability, mutations were made in a E239G, M242I, Y272F background rather than in the E239K, M242I, Y272F background previously (see WO 95/10602) thought to be the best starting point for further mutagenesis.

According to the invention a peroxidase variant with improved hydrogen peroxide stability may be obtained if the parent peroxidase, a *Coprinus cinereus* peroxidase encoded by the amino acid sequence shown in SEQ ID No. 1, has the following substitutions:

I49X+V53Y+T121Z+M166F+E239G+M242I+Y272F;
X being S, T, V, A or G; Y being G, A, S, T or H; and
Z being A, V, S, T or I; in particular
X being S or T; Y being G or A; and
Z being A or V.

In particular a peroxidase variant according to the invention may be substituted as follows:
I49S+V53A+T121A+M166F+E239G+M242I+Y272F; or
I49T+V53A+T121A+M166F+E239G+M242I+Y272F.

The above described seven mutations can be divided into interacting and non-interacting classes based on inspection of the three-dimensional structure of the enzyme.

M166, E239, M242 and Y272 are dispersed around the proximal side of the active site heme group, with no two residues lying closer than 10 angstroms from the other.

In contrast, residues I49, V53, and T121 contact each other and form the intersection of two alpha helices (helices B and D in peroxidase nomenclature) that lie on the distal side of the heme group.

Two residues involved in the catalytic mechanism, H55 and R51, lie on the opposite side of helix B from this intersection point. Mutation of these residues alters the interaction of these two critical helices, and dramatically alters the stability of the peroxidase.

The effect of additive, compatible side chain replacements at positions in this helix intersection point furthermore results in a synergistic improvement in stability (compare residual activities of variants C through H, in Example 1, Table 1 at 2 mM H2O2).

So accordingly the present invention also includes a peroxidase variant with improved hydrogen peroxide stability wherein the parent peroxidase, a *Coprinus cinereus* peroxidase encoded by the amino acid sequence shown in SEQ ID No. 1, has the following substitutions:
I49X+V53Y+T121Z;
X being S, T, V, A or G; Y being G, A, S, T or H; and
Z being A, V, S, T or I; in particular
X being S or T; Y being G or A; and
Z being A or V.

The parent peroxidase is encoded by the amino acid sequence shown in SEQ ID No. 1. Said sequence is obtainable from *Coprinus cinereus* IFO 8371.

According to the invention the parent peroxidase may be obtained as described in WO 95/10602 and the substitutions of the parent peroxidase may be done in various ways:

Once the desirable sites for mutation have been identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the peroxidase-encoding sequence, is created in a vector carrying the peroxidase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into peroxidase-encoding sequences is described in Nelson and Long, *Analytical Biochemistry* 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

According to the invention, a mutated peroxidase-coding sequence produced by one of the methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a signal sequence may be inserted prior to the peroxidase-coding sequence. For expression under the direction of control sequences, a target gene is operably linked to the control sequences in the proper reading frame. Promoter sequences that can be incorporated into plasmid vectors, and which can support the transcription of the mutant peroxidase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment, *B. subtilis* is transformed by an expression vector carrying the mutated DNA. If expression is to take place in a secreting micro-organism such as *B. subtilis*, a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when present.

The host organism transformed with the DNA sequence encoding the peroxidase variant of the invention may also be a yeast, preferably a strain of Saccharomyces, e.g. *Saccharomyces cerevisiae* or *Schizosaccharomyces pombe,* or Pichia, e.g. *Pichia pastoris.*

In a currently preferred method of producing the peroxidase variant of the invention, a filamentous fungus is used as the host organism. The filamentous fungus host organism may conveniently be one which has previously been used as a host for producing recombinant proteins, e.g. a strain of Aspergillus sp., such as *A. niger, A. nidulans* or *A. oryzae*. The use of *A. oryzae* in the production of recombinant proteins is extensively described in, e.g. EP 238 023.

For expression of peroxidase variants in Aspergillus, the DNA sequence coding for the peroxidase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a peroxidase, a cellulase or a glycolytic enzyme.

Examples of suitable promoters are those derived from the gene encoding *A. oryzae* TAKA amylase, *Rhizomucor miehei* aspartic proteinase, *A. niger* neutral a-amylase, *A. niger* acid stable a-amylase, *A. niger* glucoamylase, *Rhizomucor miehei* lipase, *A. oryzae* alkaline protease or *A. oryzae* triose phosphate isomerase.

In particular when the host organism is *A. oryzae,* a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the peroxidase variant from the host cell, the DNA sequence encoding the peroxidase variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral a-amylase, *A. niger* acid-stable a-amylase, *Coprinus cinereus* or *macrorhizus* peroxidase, or *A. niger* glucoamylase.

The medium used to culture the transformed host cells may be any conventional medium suitable for growing Aspergillus cells. The transformants are usually stable and may be cultured in the absence of selection pressure. However, if the transformants are found to be unstable, a selection marker introduced into the cells may be used for selection.

The mature peroxidase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Bleaching effect

To obtain a bleaching effect of the peroxidase variant, hydrogen peroxide or a precursor of hydrogen peroxide, preferably perborate or percarbonate, or a hydrogen peroxide generating enzyme system, e.g., an oxidase and its substrate, or a peroxycarboxylic acid or a salt thereof, should be present in the bleaching composition of the invention as substrate for the peroxidase variant.

By using a peroxidase variant according to the invention which is less sensitive to hydrogen peroxide, it may be possible to add a smaller amount of the enzyme to the bleaching/washing liquor and yet obtain a satisfactory bleaching effect.

In the bleaching composition, the amount of peroxidase variant corresponds to a concentration in the wash liquor of 0.01–100 mg enzyme protein per liter, in particular 0.1–10 mg enzyme protein per liter, and the amount of hydrogen peroxide or hydrogen peroxide precursor or hydrogen peroxide generating enzyme system or percarboxylic acid or a salt thereof corresponds to a hydrogen peroxide concentration of up to 20 mM $H_2O_2$.

Oxidizable substrates

For use of the present peroxidase variants for bleaching reactions, it has been found that the addition of another oxidizable substrate (for the peroxidase variants of the invention) at the beginning or during the washing and/or rinsing process may enhance the bleaching effect of the peroxidase variant employed.

Examples of such oxidizable substrates are organic compounds such as phenolic compounds, e.g. p-hydroxybenzenesulfonate. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., *Peroxidase,* London, 1964, p. 141 ff.

In WO 94/12621 other types of enhancing agents are disclosed which may be used for the present purpose, e.g. phenothiazines or phenoxazines or derivatives thereof such as 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propyl-phenothiazine, 10-isopropylphenothiazine, methyl-10-phenothiazinepropionate, 10-phenylphenothiazine, 10-allylphenothiazine, 10-(3-(4-methyl-1-piperazinyl) propyl)phenothiazine, 10-(2-pyrrolidinoethyl) phenothiazine, promazine, 2-chloro-10-methylphenothiazine, 2-acetyl-10-methylphenothiazine or 10-methylphenoxazine.

In WO 96/10079 another group of enhancing agents are disclosed which may be used for the present purpose, e.g., acetosyringone, syringaldehyde, methylsyringate or syringic acid.

The amount of oxidizable substrate corresponds to a concentration in the wash liquor of between 0.1 $\mu$M and 100 $\mu$M.

Detergent Compositions

The detergent compositions according to the present invention comprise a surfactant system, wherein the surfactant can be selected from nonionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepa™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

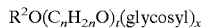

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof. Highly preferred nonionic surfactants are polyhydroxy fatty acid amide surfactants of the formula

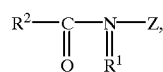

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulphate surfactants. Examples hereof are water soluble salts or acids of the formula $RO(A)_mSO3M$ wherein R is an unsubstituted $C_{10}$–$C_{24}$-alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulphates as well as alkyl propoxylated sulphates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulphate ($C_{12}$–$C_{18}$E(1.0)M) $C_{12}$–$C_{18}$ alkyl polyethoxylate (2.25) sulphate ($C_{12}$–$C_{18}$(2.25)M, and $C_{12}$–$C_{18}$ alkyl polyethoxylate (3.0) sulphate ($C_{12}$–$C_{18}$E(3.0)M), and $C_{12}$–$C_{18}$ alkyl polyethoxylate (4.0) sulphate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

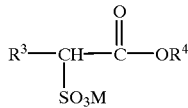

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2OO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

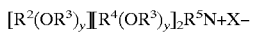

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2$CHOHCHOHCOR$^6$CHOHCH$_2$OH, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

  (i)

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{4O})$H where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:
coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12}$–$C_{15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

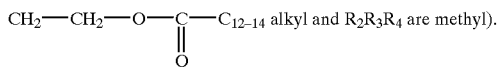

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

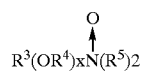

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder system

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme (s) which provides cleaning performance and/or fabric care benefits.

Such enzymes include proteases, lipases, cutinases, amylases, cellulases, peroxidases, oxidases (e.g. laccases). Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (α and/or β) suitable for use in alkaline solutions can be used. Suitable amylases include those of bacterial or fungal origin. Chemically or genetically modified mutants are included. Amylases include, for example, α-amylases obtained from a special strain of *B. licheniformis,* described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens.* Especially suitable cellulases are the cellulases having colour care benefits. Examples of such cellulases are cellulases described in European patent application No. 0 495 257.

Commercially available cellulases include Celluzyme™ produced by a strain of *Humicola insolens,* (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase, a cellulase and a peroxidase variant according to the invention.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents: Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483, 781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds suppressors: Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/ silica mixture in combination with fumed nonporous silica such as Aerosil$^R$.

The suds suppressors described above are normally employed at levels of from 0.001% to 2% by weight of the composition, preferably from 0.01% to 1% by weight.

Other components: Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4 -(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2'disulphonate, di-so-dium 4,4'bis(2-anilino-4-(1-methyl-2-hydroxyethylamino)-s-triazin-6-ylami -no)stilbene-2,2'disulphonate, sodium 2(stilbyl-4"-(naphtho -1',2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

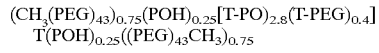

where PEG is —(OC$_2$H$_4$)0—, PO is (OC$_3$H$_6$O) and T is (pOOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents: Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents: The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. from 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1x}$–$C_{1y}$ alkyl sulfate
SS: Secondary soap surfactant of formula 2-butyl octanoic acid
25EY: A $C_{12}$–$C_{15}$ predominantly linear primary alcohol condensed with an average of Y moles of ethylene oxide
45EY: A $C_{14}$–$C_{15}$ predominantly linear primary alcohol condensed with an average of Y moles of ethylene oxide
XYEZS: $C_{1x}$–$C_{1y}$ sodium alkyl sulfate condensed with an average of Z moles of ethylene oxide per mole
Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh
CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula $\delta$-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12}$. $27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N,N'-disuccinic acid, [S,S] isomer in the form of the sodium salt
Suds 25% paraffin wax Mpt 50° C., 17% hydrophobic silica, 58%

Suppressor: paraffin oil
Granular Suds 12% Silicone/silica, 18% stearyl alcohol, 70%
suppressor: starch in granular form
Sulphate: Anhydrous sodium sulphate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

The present invention is further illustrated in the following example which is not in any way intended to limit the scope of the invention as claimed.

EXAMPLE 1

Construction of Coprinus cinereus peroxidase (CiP) random mutant libraries:

The CiP gene was mutagenized much as previously described in WO 95/10602. Briefly, a plasmid containing the entire CiP coding sequence was used as a template for mutagenic PCR amplification. Amplifications were performed in reactions containing the primers CiPpcrdwn (5' CTGGGGTAATTAATCAGCGAAGCGATG) and pYES2-seq (5' GGGCGTGAATGTAAGCGTGAC), 1X Mn PCR buffer (10X buffer containing 0.1M Tris, pH 8.3, 0.5 M KCl, 0.1% gelatin, 3 mM MgCl$_2$, 0.3 mM MnCl$_2$) and 0.2 mM each dGTP, dTTP, dCTP, and 0.04 mM dATP. Resulting PCR products containing the entire CiP coding sequence was then transformed by electroporation directly into yeast strain YNG344 (derived from S. cerevisiae JC842, Cannon and Tatchell (1987) Mol. Cell. Biol. 7:2653–2663) with a gapped CiP yeast expression plasmid, with the gap covering the codons mutagenized.

Construction of localized random libraries:

Mutations to specific residues were made using the 3-primer PCR method as described WO 95/10602. PCR fragments were transformed by electroporation directly into yeast with a gapped CiP yeast expression plasmid, with the gap covering the codons mutagenized. This technique has been described previously by Muhlrad et al. (Yeast (1992) 8:79–82).

In vivo recombination of interesting mutants: Shuffling of DNA fragments:

Mutants containing multiple point mutations were shuffled using gap repair in yeast. Yeast transformants that demonstrated good stability (see below) were pooled and plasmid DNA was purified as described by Kaiser and Bauer (1993) BioTechniques 14:552 except that the rescued plasmid was not transferred into E. coli but used directly as template for non-mutagenic PCR. The resulting DNA fragments, containing a mix of mutant CiP genes, were then transformed directly into yeast by gap-repair. During transformation, the robust yeast recombination system shuffles the genes, randomizing the combination of various point mutations.

High pH/Thermal Stability Screening:

Growth and screening of mutants is performed using a robotic 96-well system. The 96-well plate screen is performed by first growing yeast transformants of a pool of mutants in 50 μL volumes of URA(–) medium, pH 6.0 in 96-well microtiter plates. Cultures are inoculated by dilution into medium and pipetting (robotic or manual autopipettor) into 96-well plates. These are placed in a special adapter in an Inova 4000 incubator set at 30° C., 350 RPM and shaken for approximately 5 days.

Culture broths are assayed for 'initial activity', diluted, inactivated by incubation in the presence of various levels of hydrogen peroxide, then re-assayed to allow calculation of a 'residual activity'. Specifically, 180 μl of substrate buffer {120 ml of 0.1 M potassium phosphate-0.01% Tween-80 pH 7.0, 250 μl of 2,2'-azinobis(3-ethylbenzothiazoline-6-sulfonate) (ABTS) solution (22 mg/ml), and 2 μl of 30% hydrogen peroxide} are added to 20 μl of culture supernatant which has been suitably diluted in 0.1 M potassium phosphate-0.01% Tween-80 pH 7.0 buffer, quickly followed by measurement of the absorbance at 405 nm at 25° C. using a Molecular Devices Thermomax Microplate Reader (Molecular Devices, Sunnyvale, Calif.). Measurements are recorded every 10 seconds over a 2 minute period with mixing and $V_{max}$ values are calculated using the SOFTmax program (Molecular Devices, Sunnyvale, Calif.). The peroxidase units per ml are estimated using a standard curve constructed with a known amount of Cinereus coprinus peroxidase as a standard:

Determination of peroxidase activity in the standard:

One peroxidase unit is the amount of enzyme which under the following conditions catalyze the conversion of 1 μmole hydrogen peroxide per minute:

0.1 M phosphate buffer pH 7.0
0.88 mM hydrogen peroxide
1.67 mM 2,2'-azino-bis(3-ethylbenzothiazoline-6-sulfonate) (ABTS)
30° C.

The reaction is followed for 60 seconds (15 seconds after mixing) by the change in absorbance at 418 nm, which should be in the range 0.15 to 0.30.

For calculation of activity an absorption coefficient of oxidized ABTS of 36 mM$^{-1}$ cm$^{-1}$ is used and a stoichiometry of one μmole H$_2$O$_2$ converted per two μmole ABTS oxidized.

Based on an initial screening using this assay, broths were selected and tested in a new assay, where the broths were diluted to 0.06 peroxidase units ml and incubated in various concentrations of hydrogen peroxide (200 μM to 15 mM), 100 mM phosphate/borate buffer, pH 10 at 50° C. After 0, 10, and 20 minutes, samples are removed and activity is measured using the ABTS assay, pH 7.0, described above. Residual activity is calculated by dividing the measured residual activity by the initial activity and multiplying by 100.

Results and Discussion:

Table 1 summarizes the results of residual activity assays on the best variants obtained after the screening of approximately 200,000 independent yeast clones. While initial rounds of mutagenesis relied on the introduction of point mutations using manganese-poisoned PCR, final rounds were conducted by shuffling of selected mutants to identify the best combinations of point mutations for improved stability.

The dramatic improvement (variant A) in peroxidase stability can be attributed to a synergistic effect of seven mutations: I49S, V53A, T121A, M166F, E239G, M242I, and Y272F. A variant with nearly equivalent stability, variant B, contains a nearly identical combination of amino acid substitutions except that I49 is substituted with T rather than S.

TABLE 1

% Residual Activity after treatment for 20 minutes, 50° C., pH 10 with varying H$_2$O$_2$ (mM)

| | H$_2$O$_2$ Concentration | | | | | |
|---|---|---|---|---|---|---|
| | 0.0 | 0.2 | 2.0 | 5.0 | 10.0 | 15.0 |
| A | 104 | 100 | 90 | 71 | 59 | 39 |
| B | 103 | 92 | 78 | 53 | 37 | 19 |
| C | 101 | 96 | 75 | 53 | 21 | 5 |
| D | — | 97 | 41 | — | — | — |
| E | | 82 | 39 | | | |
| F | — | 80 | 38 | — | — | — |
| G | — | 19 | 23 | — | — | — |
| H | — | 66 | 11 | — | — | — |
| I | 78 | 58 | 1 | 1 | 0 | 0 |
| J | 88 | 35 | 0 | 0 | 0 | 0 |
| K | 0 | 0 | 0 | 0 | 0 | 0 |

In Table 1 the following abbreviations are used:
A = I49S + V53A + T121A + M166F + E239G + M242I + Y272F;
B = I49T + V53A + T121A + M166F + E239G + M242I + Y272F;
C = I49S + V53A + T121A + E239G + M242I + Y272F;
D = I49T + V53A + E239G + M242I + Y272F;
E = V53A + T121A + E239G + M242I + Y272F;
F = V53A + E239G + M242I + Y272F;
G = T121A + E239G + M242I + Y272F;
H = I49T + E239G + M242I + Y272F;
I = M166F + E239G + M242I + Y272F;
J = E239G + M242I + Y272F;
K = wild type, no mutations.

EXAMPLE 2

Washing trials

To investigate the stability of CiP (*Coprinus cinereus* peroxidase) and mutants thereof disclosed in the present application, washing trials may be performed in which the dye transfer inhibition (DTI) properties of the enzymes are evaluated under conditions of high hydrogen peroxide levels, high pH and elevated temperature. Usually the peroxidase is combined with a second oxidizable substance (a mediator or enhancer) as disclosed in WO 91/05839; WO 94/12621 and WO 96/00179.

In a trial of this kind, mutants
67: E239K+M242I+Y272F;
70: M166F+E239K+M242I+Y272F;
105: I49S+V53A+T121A+M166F+E239G+M242I+Y272F; and
106: I49S+V53A+T121A+M166F+E239G+M242I+Y272F;
were tested.

The detergent was the commercially available bleach-containing powder detergent Ariel Futur (purchased in Denmark 1997, ex Procter and Gamble), here dosed to 4 grams/l washing liquor, prepared using tap water (18° dH hardness). The wash was carried out in open beakers with magnetic stirring, isothermally at 40° C., for 15 min. The dye transfer test system used was bleeding cotton fabric dyed with Direct Blue 1 (ex Textile Innovators) and, as tracer fabric, bleached cotton style #400 ex Testfabrics Inc. with no optical brightener added.

The enzymes were dosed to two levels, 0.2 mg/l and 0.4 mg/l, on the basis of the absorbance of the stock solutions at 404 nm, assuming the relation
1 mg peroxidase/ml~A(404 nm)=2.87
to hold.

As mediator, phenothiazine-10-propionic acid was used together with each of the enzymes, each time dosed to a level of 10 μM.

At the end of the washes, pH was generally measured to be approximately 9.8. The level of hydrogen peroxide equivalents in the washing liquor was estimated, from iodometric titrations on samples withdrawn after 5 min (to ensure complete dissolution of the hydrogen peroxide source from the detergent) in corresponding solutions prepared at ambient temperature, to be 7.1±0.3 mM.

After being rinsed in cold water and air-dried in the dark overnight, the tracer fabric swatches were measured in a ColorEye 7000 reflectometer (with the exclusion of UV light) to obtain Hunter color difference (ΔE) readings.

The washing results obtained were:

| Enzyme | Hunter ΔE with respect to separately washed tracer fabric | |
|---|---|---|
| No enzyme, no mediator (reference) | 17.7 | |
| No enzyme; with mediator at 10 μM | 17.3 | |
| | 0.2 mg/l | 0.4 mg/l |
| CiP | 15.4 | 13.4 |
| 67 | 14.3 | 13.1 |
| 105 | 13.9 | 10.0(*) |
| 70 | 12.1 | 9.6 |
| 106 | 12.2 | 8.2 |

(The results are averages of duplicate executions except for (*), which was a single execution. The deviations between duplicates were generally less than one ΔE unit.)

It is seen that the order of performance benefits obtained (i.e. of lowering of the reference discoloration of 17.7 ΔE units) was CiP<67<105<70<106, with the last three mutants providing significant DTI under these stressed conditions. (Mutant 67 is the variant disclosed in WO 95/10602 having the best hydrogen peroxide stability). So this Example shows that we have indeed created variants of the enzyme with surprisingly improved stability towards hydrogen peroxide under alkaline conditions.

We claim:

1. A peroxidase variant with improved hydrogen peroxide stability as compared to the parent peroxidase, wherein the following residues of the parent peroxidase, a *Coprinus cinereus* peroxidase encoded by the amino acid sequence shown in SEQ ID No. 1, are substituted as follows:

I49X+V53Y+T121Z+M166F+E239G+M242I+Y272F; or
I49X+V53Y+T121Z;

X being S, T, V, A or G; Y being G, A, S, T or H; and Z being A, V, S, T or I.

2. A peroxidase variant according to claim 1 wherein the variant has the following substitutions:
I49S+V53A+T121A+M166F+E239G+M242I+Y272F.

3. A peroxidase variant according to claim 1 wherein the variant has the following substitutions:
I49T+V53A+T121A+M166F+E239G+M242I+Y272F.

4. A bleaching composition comprising a peroxidase variant according to claim 1 and hydrogen peroxide or a hydrogen peroxide precursor.

5. A bleaching composition according to claim 4, wherein the hydrogen peroxide precursor is perborate, percarbonate, or a hydrogen peroxide generating enzyme system.

6. A bleaching composition according to claim 5 wherein the hydrogen peroxide generating enzyme system is an oxidase and its substrate.

7. A bleaching composition according to claim 4, wherein the hydrogen peroxide precursor is a peroxycarboxylic acid or a salt of a peroxycarboxylic acid.

8. A bleaching composition according to claim 4, wherein the amount of peroxidase variant corresponds to a concentration in the wash liquor of 0.01–100 mg enzyme protein per liter, and the amount of hydrogen peroxide or hydrogen peroxide precursor or hydrogen peroxide generating enzyme system or peroxycarboxylic acid or a salt thereof corresponds to a hydrogen peroxide concentration in the wash liquor of up to 20 mM $H_2O_2$.

9. A bleaching composition according to claim 4, which additionally comprises an oxidizable substrate.

10. A bleaching composition according to claim 9, wherein the amount of oxidizable substrate corresponds to a concentration in the wash liquor of between 0.1 $\mu$M and 100 $\mu$M.

11. A detergent composition comprising a surfactant, a peroxidase variant according to claim 1 and hydrogen peroxide or a hydrogen peroxide precursor.

12. A detergent composition according to claim 11, wherein the hydrogen peroxide precursor is perborate, percarbonate, or a hydrogen peroxide generating enzyme system.

13. A detergent composition according to claim 12, wherein the hydrogen peroxide generating enzyme system is an oxidase and its substrate.

14. A detergent composition according to claim 11, wherein the hydrogen peroxide precursor is a peroxycarboxylic acid or a salt of a peroxycarboxylic acid.

15. A detergent composition according to claim 11, wherein the amount of peroxidase variant corresponds to a concentration in the wash liquor of 0.01–100 mg enzyme protein per liter, and the amount of hydrogen peroxide or hydrogen peroxide precursor or hydrogen peroxide generating enzyme system or peroxycarboxylic acid or a salt thereof corresponds to a hydrogen peroxide concentration in the wash liquor of up to 20 mM $H_2O_2$.

16. A detergent composition according to claim 11, which additionally comprises an oxidizable substrate.

17. A detergent composition according to claim 16, wherein the amount of oxidizable substrate corresponds to a concentration in the wash liquor of between 0.1 $\mu$M and 100 $\mu$M.

18. A peroxidase variant with improved hydrogen peroxide stability as compared to the parent peroxidase at alkaline conditions, wherein the residues 49, 53 121, 166, 239, 242 and 272 of the parent peroxidase, a *Coprinus cinereus* peroxidase encoded by the amino acid sequence shown in SEQ ID No. 1, are substituted as follows:

I49X+V53Y+T121Z+M166F+E239G+M242I+Y272F;

X being S, T, V, A or G; Y being G, A, S, T or H; and Z being A, V, S, T or I.

* * * * *